(12) United States Patent
Sun et al.

(10) Patent No.: US 11,156,453 B2
(45) Date of Patent: *Oct. 26, 2021

(54) WATER-IMMERSED HIGH PRECISION LASER FOCUS SPOT SIZE MEASUREMENT APPARATUS

(71) Applicant: AMO DEVELOPMENT, LLC, Santa Ana, CA (US)

(72) Inventors: Zheng Sun, San Jose, CA (US); Daniel Bray, Milpitas, CA (US); Zenon Witowski, Pleasanton, CA (US); Timothy Slotterback, Trabuco Canyon, CA (US); Hong Fu, Pleasanton, CA (US)

(73) Assignee: AMO Development, LLC, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/907,105

(22) Filed: Jun. 19, 2020

(65) Prior Publication Data
US 2020/0318952 A1 Oct. 8, 2020

Related U.S. Application Data

(62) Division of application No. 16/027,137, filed on Jul. 3, 2018, now Pat. No. 10,690,486.

(51) Int. Cl.
*G01B 11/24* (2006.01)

(52) U.S. Cl.
CPC .............................. *G01B 11/2408* (2013.01)

(58) Field of Classification Search
CPC .............. G01N 21/95; G01N 21/8806; G01N 2201/0675; H01L 21/67288;
(Continued)

(56) References Cited

U.S. PATENT DOCUMENTS

| 4,917,489 A | 4/1990 | Nishio et al. |
| 5,870,223 A | 2/1999 | Tomimatsu |

(Continued)

OTHER PUBLICATIONS

Karpiouk A.B., et al., "Quantitative Ultrasound Method to Detect and Monitor Laser-induced Cavitation Bubbles," Journal of Biomedical Optics, May-Jun. 2008, vol. 13 (3), pp. 034011.
(Continued)

*Primary Examiner* — Sang H Nguyen
(74) *Attorney, Agent, or Firm* — Johnson & Johnson Surgical Vision, Inc.

(57) ABSTRACT

A measurement apparatus for measuring a laser focus spot size, which includes a two-dimensional image detector and an imaging system which forms a magnified image of a focus spot located an object plane onto the image detector. The imaging system includes at least an objective lens. A sealed liquid container is secured over a part of the objective lens such as the optical surface of the objective lens is immersed in the liquid (e.g. water) within the container. The liquid container has a window through which the laser beam enters. An image processing method is also disclosed which processes the image obtained by the image detector to obtain the focus spot size while implementing an algorithm that corrects for the effect of ambient vibration.

7 Claims, 4 Drawing Sheets

(58) Field of Classification Search
CPC ......... H01L 21/02636; H01L 21/02532; H01L 22/12; H01L 27/11582; H01L 27/11556; G06F 17/5018; G06F 2217/16; G02B 27/0012; G01B 11/2408
See application file for complete search history.

(56) References Cited

U.S. PATENT DOCUMENTS

| | | | |
|---|---|---|---|
| 6,720,547 B1* | 4/2004 | Rajadhyaksha | G01N 21/21 250/208.1 |
| 7,101,356 B2 | 9/2006 | Miller | |
| 7,101,365 B1* | 9/2006 | Sharon | A61B 18/203 606/9 |
| 7,139,122 B1* | 11/2006 | Eastman | A61K 49/001 359/386 |
| 7,995,272 B2* | 8/2011 | Bratt | G02B 21/02 359/391 |
| 8,169,591 B2* | 5/2012 | Owa | G03F 7/70341 355/30 |
| 8,431,903 B2 | 4/2013 | Duhr et al. | |
| 8,853,650 B2 | 10/2014 | Duhr et al. | |
| 9,291,546 B2* | 3/2016 | Nakasho | G01N 21/01 |
| 9,694,447 B1 | 7/2017 | Hughes et al. | |
| 9,971,139 B2* | 5/2018 | Fujioka | G02B 21/12 |
| 10,120,179 B2* | 11/2018 | Brinkman | G02B 21/24 |
| 10,634,888 B2* | 4/2020 | Lippert | G02B 21/025 |
| 10,746,978 B2* | 8/2020 | Brinkman | G02B 21/33 |
| 2004/0040379 A1 | 3/2004 | O'Donnell et al. | |
| 2005/0121596 A1 | 6/2005 | Kam et al. | |
| 2009/0086314 A1 | 4/2009 | Namba et al. | |
| 2009/0168061 A1* | 7/2009 | Haga | G01N 21/6428 356/317 |
| 2009/0213369 A1 | 8/2009 | Lee et al. | |
| 2010/0111768 A1* | 5/2010 | Banerjee | C12Q 1/6869 422/82.08 |
| 2010/0118395 A1* | 5/2010 | Douglas-Hamilton | G02B 27/141 359/385 |
| 2010/0245816 A1 | 9/2010 | Shen et al. | |
| 2013/0056910 A1 | 3/2013 | Houbertz-Krauss et al. | |
| 2013/0210027 A1 | 8/2013 | Boisen et al. | |
| 2016/0143589 A1 | 5/2016 | Kabetani et al. | |
| 2017/0112663 A1* | 4/2017 | Bareket et al. | |

OTHER PUBLICATIONS

Karpiouk, A.B., et al., "Ultrasound Visualization of Internal Crystalline Lens Deformation Using Laser-Induced Microbubbles," Proceedings of SPIE, Feb. 2014, vol. 8946, pp. 12.

Mallidi S., et al., "Photoacoustic Technique to Measure Beam Profile of Pulsed Laser Systems," Review of Scientific Instruments, May 2009, vol. 80 (5), pp. 054901.

* cited by examiner

US 11,156,453 B2

WATER-IMMERSED HIGH PRECISION LASER FOCUS SPOT SIZE MEASUREMENT APPARATUS

CROSS REFERENCE TO RELATED APPLICATIONS

This application is a divisional of and claims priority to U.S. patent application Ser. No. 16/027,137, filed Jul. 3, 2018, which is incorporated herein by reference in its entirety.

BACKGROUND OF THE INVENTION

Field of the Invention

This invention relates to a measurement apparatus for measuring a laser focus spot size for a laser ophthalmic surgical system, and in particular, it relates to such a measurement apparatus for measuring a laser focus spot located in water or another liquid.

Description of Related Art

Laser ophthalmic surgical systems use a laser device to generate a pulsed or continuous laser beam, and use a beam delivery optical system to focus the laser beam to a highly focused light spot and deliver the laser focus spot in target tissues of the eye to effectuate various types of treatments of the eye. In many laser ophthalmic surgical systems, the laser device generates a pulsed laser beam having ultra-short pulse lengths in the range of femtoseconds to nanoseconds, and the beam is focused to a focus spot size as small as 1 μm or less. A scanning device of the beam delivery system scans the laser focus spot inside the eye tissue to form incisions in the tissue. In such laser surgical systems, the laser focus spot size in the eye is a critical parameter that determines the tissue incision quality such as precision of the incision. Spot size is also a critical parameter for designing laser spot scan patterns that avoid collateral damage to eye tissues to ensure patient safety.

Conventionally, the laser focus spot size of a laser system can be determined either by directly measuring it using a spot size camera, where the laser beam shines directly on the camera, or by indirectly deriving it from wavefront measurements of the light beam. In both techniques, the laser focus spot in placed in the air, i.e., the laser spot is focused to a point in a volume of air or on a detector surface of the camera that is disposed in air. It is difficult to use conventional measurement techniques to measure laser focus spot sizes smaller than about 1 mm.

SUMMARY

Accordingly, the present invention is directed to a laser focus spot measurement apparatus and related method that substantially obviates one or more of the problems due to limitations and disadvantages of the related art.

An object of the present invention is to provide an easy to use apparatus that allows for measurement of laser focus spot in water or another liquid.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a measurement apparatus for measuring a laser focus spot size, which includes: a two-dimensional image detector having a detecting surface; an imaging system including at least an objective lens, the imaging system being disposed in front of the image detector and configured to form a magnified image of an object located on an object plane onto the detecting surface of the image detector; and a sealed liquid container containing a liquid, the container including a flexible body with a transparent window and an opening, wherein the objective lens is partially disposed through the opening and joined to the body in a liquid-tight seal, and wherein a front optical surface of the objective lens is exposed to the liquid inside the container.

In one embodiment, the body of the container includes a bellows which is formed of rubber of a flexible plastic material. The transparent window includes a rigid frame and a transparent plate joined to the frame, the rigid frame being disposed through another opening in the flexible body and joined to the body in a liquid-tight seal.

In one embodiment, the imaging system uses an infinite correction configuration which uses another lens in addition to the objective lens.

In another aspect, the present invention provides a measurement apparatus for measuring a laser focus spot size, which includes: a two-dimensional image detector having a detecting surface; an imaging system including at least an objective lens, the imaging system being disposed in front of the image detector and configured to form a magnified image of an object located on an object plane onto the detecting surface of the image detector; and a liquid container containing a liquid and joined to the objective lens, wherein a front optical surface of the objective lens is exposed to the liquid inside the container.

In another aspect, the present invention provides a measurement apparatus for measuring a laser focus spot size, which includes: a two-dimensional image detector having a detecting surface; an imaging system including at least an objective lens, the imaging system being disposed in front of the image detector and configured to form a magnified image of an object located on an object plane onto the detecting surface of the image detector; and a data processing device coupled to the image detector, configured to process image data generated by the image detector, the data processing device being configured to: receive image data representing an image of a light beam focus spot; calculate a centroid of the focus spot; determine whether the centroid is located at a predetermined center position; when the centroid is located at the predetermined center position, store the image in an image buffer; when the centroid is not located at a predetermined center position, define a region of interest (ROI) of the image containing the focus spot and extract the ROI to a new image, the new image containing the focus spot centered at the predetermined center position, and store the new image in the image buffer; and analyze the images in the image buffer to calculate a size of the light beam focus spot.

In another aspect, the present invention provides a method implemented in a measurement apparatus for measuring a laser focus spot size, where the measurement apparatus includes a two-dimensional image detector, an imaging system configured to form a magnified image of an object located on an object plane onto the detecting surface of the image detector, and a data processing device coupled to the image detector, where the data processing device performs the following method: receiving image data representing an image of a light beam focus spot; calculate a centroid of the focus spot; determining whether the centroid is located at a predetermined center position; when the centroid is located at the predetermined center position, storing the image in an image buffer; when the centroid is not located at a predetermined center position, defining a region of interest (ROI) of the image containing the focus spot and extracting the ROI to a new image, the new image containing the focus spot centered at the predetermined center position, and storing the new image in the image buffer; and analyzing the images in the image buffer to calculate a size of the light beam focus spot.

It is to be understood that both the foregoing general description and the following detailed description are exemplary and explanatory and are intended to provide further explanation of the invention as claimed.

DETAILED DESCRIPTION OF PREFERRED EMBODIMENTS

Measuring the laser focus spot size is a critical task when developing a beam delivery optical system of a laser surgical system, as well as when operating or maintaining the laser surgical system. Conventional laser focus spot size measurement techniques cannot satisfy the requirements of high quality laser ophthalmic surgical systems. For example, in conventional techniques for measuring laser focus spot size, the laser beam is focused in the air. However, for a high numerical aperture (NA) beam delivery system, for example, one with NA≥0.4, the placement of the laser focus spot in the air introduces wavefront distortions that do not exist when the laser focus is under surgical conditions, i.e. when the laser focus is located inside an eye tissue. The inventors recognized that such distortions can be excessive and undesirable when the system has an NA≥0.5, or when NA=0.4 but the focus spot is relatively deep in the air, such as approximately 1 mm beyond the distal surface of the focusing objective lens of the beam delivery optical system.

Embodiments of the present invention provide a measurement apparatus for measuring the laser focus quality in the eye. The measurement apparatus enables measurement of the laser focus spot size in water, which resembles tissues in the eye. The apparatus may be used to assess the performance of high numerical aperture beam delivery system of a surgical femtosecond laser system or other laser systems.

The laser focus spot size measurement apparatus according to embodiments of the present invention has the following characteristics.

The measurement apparatus places the laser focus spot into water when measuring the focus spot size, since the refractive index of eye tissues in the visual field (e.g., about 1.37 for cornea) is close to that of water (1.33). This is accomplished by using water-immersed spot size measurement optics. Preferably, the optics adopt an infinite imaging optical design to minimize the aberration and to optimize the precision of the measurement.

The measurement apparatus includes a flexible water container/interface device, which can conveniently couple the laser focus spot into the object plane of the water-immersed spot size measurement optics.

Further, to accurately measure spot size on the order of 1 μm under normal ambient vibration levels, an image processing algorithm and system are provided to overcome the effect of vibration movement between the laser focus spot and the spot size measurement optics. This enables practical applications of the measurement apparatus.

Figure 1:
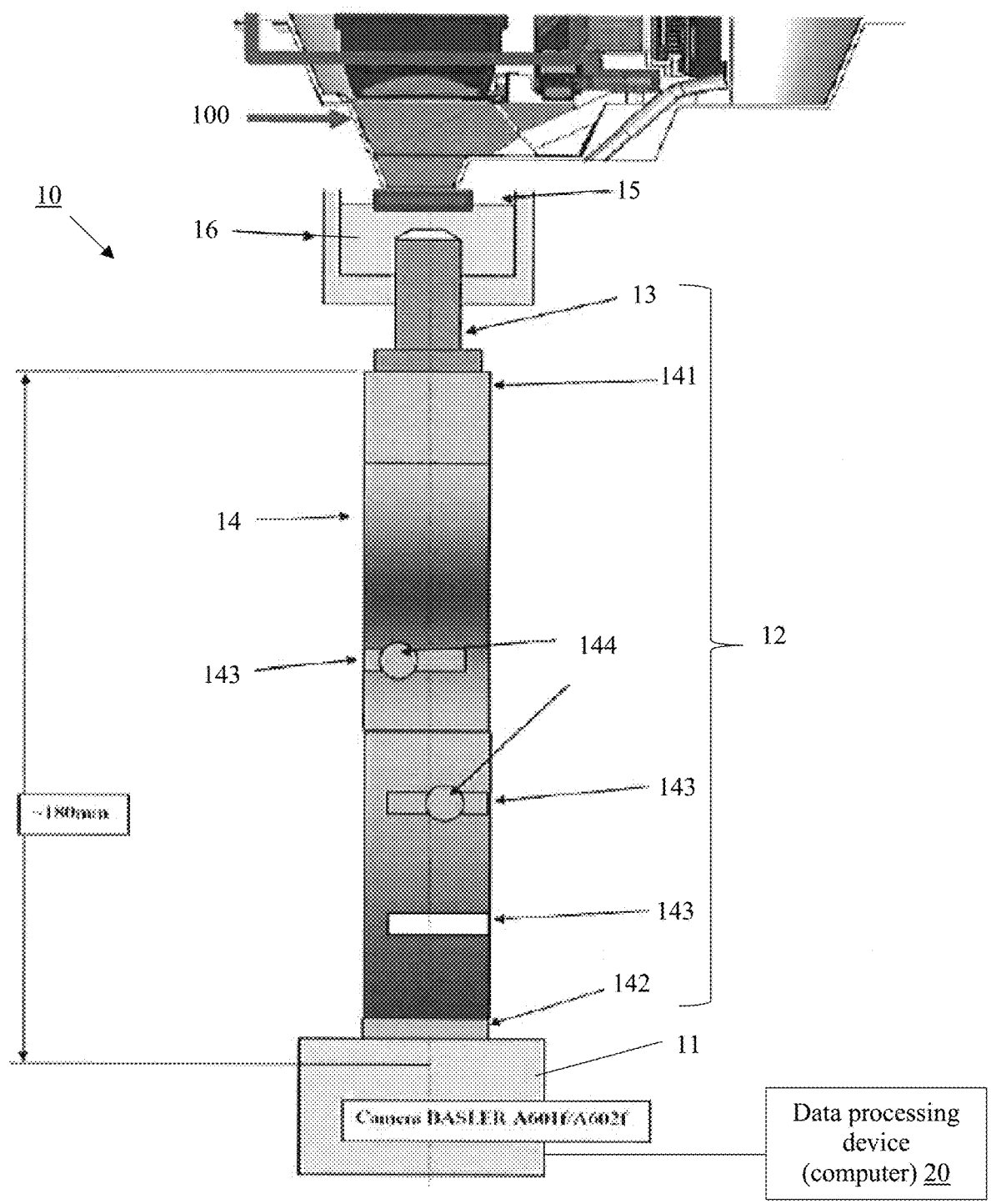
FIG. 1 illustrates the overall structure of a water-immersed laser focus spot size measurement apparatus according to an embodiment of the present invention.

The overall structure of a water-immersed laser focus spot size measurement apparatus is illustrated in FIG. 1. The measurement apparatus 10 includes a two-dimensional optical image detector 11 (also referred to as a camera), and an optical assembly (imaging system) 12 which is disposed in front of the detector and configured to form a magnified image of an object (such as a laser focus spot) located on an object plane onto the detecting surface of the detector. The detector 11 detects the size and shape of the image of the laser focus spot. The imaging system 12 includes at least one objective lens 13 located at the upstream end of the optical path. The objective 13 is mounted on a housing 14 which contains other optical components of the imaging system; the detector 11 is also mounted on the housing. A portion of the beam delivery optical system 100 which delivers the laser focus spot is also shown in FIG. 1. While in the illustrated embodiment the laser beam is delivered in the vertical direction, in other embodiments it may be in the horizontal direction.

In the illustrated embodiment, the housing 14 is a cylindrical tube with the objective 13 and the detector 12 mounted at two opposite ends of the tube, via adapters 141 and 142, respectively. In alternative embodiments, the optical path of the imaging system may fold inside the housing, and the objective 13 and the detector 12 are located at the two ends of the optical path but may be mounted at any suitable physical locations on the housing. The tube 14 may be conveniently provided with slots 143 for inserting desired optical components such as filters, waveplates, polarizers, etc. into the optical path of the imaging system. FIG. 1 also shows handle screws 144 associated with some slots.

The measurement apparatus 10 also includes a water (liquid) container 15 physically attached to the objective 13 such that the outer optical surface of the objective is exposed to the liquid 16. The liquid completely fills the space between the last optical surface of the laser beam delivery system 100 and the outer surface of the objective 13. In other words, there laser beam propagates from the laser beam delivery system 100 to the objective 13 without passing through air. The structure of the liquid container 15 will be described in more detail later.

Figure 2:
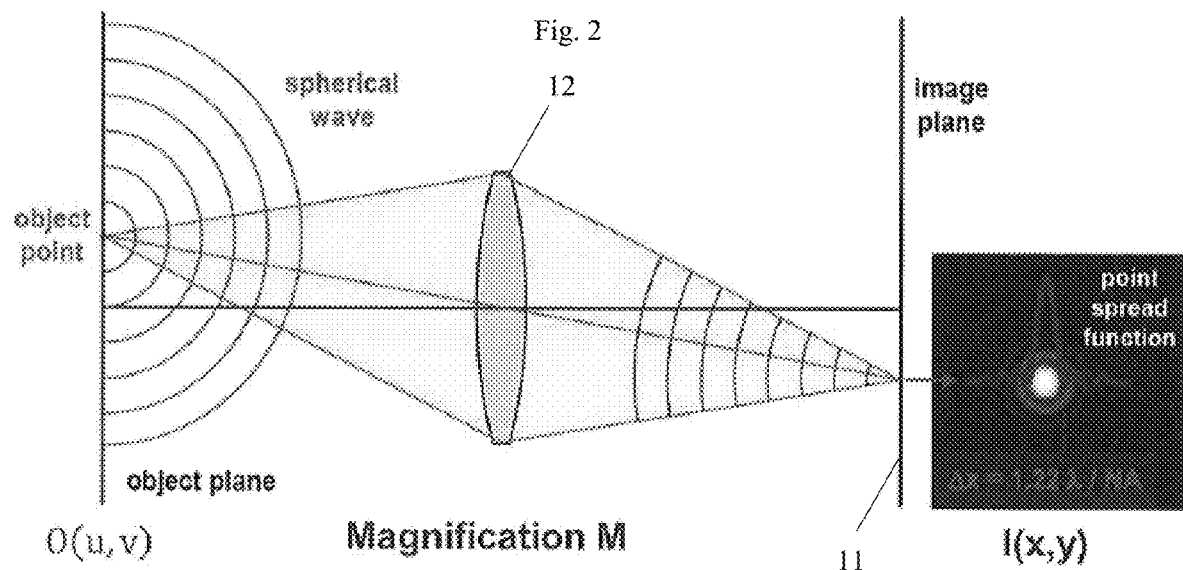
FIG. 2 schematically illustrates the working principle of laser focus spot measurement according to embodiments of the present invention.

FIG. 2 schematically illustrates the working principle of laser focus spot measurement. As shown in FIG. 2, the laser beam is focused to a position located on an object plane O. The object point represents a point in the laser focus spot that emits light. The imaging system 12, schematically depicted as a lens, images the points on the object plane O to points on the image plane of the detector 11, with a magnification M. The image formation of the imaging system 12 may be represented by a convolution of the object on the object plane with a point spread function (PSF). The PSF of a given imaging system may be calculated by numerical modeling based on parameters of the optical components within the imaging system. For a laser focus spot with known size and shape, the corresponding image spot size and shape at the imaging plane of the detector 11 can be calculated from the PSF and magnification of the given imaging system 12. Conversely, from a measured image spot size and shape at the imaging plane of the detector 11, the object size and shape at the object plane may be calculated using deconvolution.

The PSF and magnification of the imaging system 12 may also be obtained empirically using a calibration process, by imaging objects having known sizes, such as slits with known widths illuminated by a light source.

When the focus spot size is comparable to the wavelength of the laser light, the imaging system should have very small aberration, with a Strehl ratio close to 1, so that the convolution with the SPF will not distort the image. Also, the imaging system 12 preferably has a larger NA than that of the laser beam delivery system, so as to collect substantially all spatial information of the laser light. In preferred embodiments, the NA of the imaging system 12 (i.e., of the objective 13) is between 0.7 and 1.0, although other values may also be used. The objective 13 of the imaging system 12 preferably has a lateral magnification between 50× and 100×, although other values may also be used.

The image detector 11 is a 2-dimensional detector with sufficient spatial resolution (pixel size) to adequately detect the shape of the image of the focus spot. In some embodiments, the image detector has a pixel size of 5 μm or less.

The imaging system 12 may employ either an infinite correction configuration or a finite correction configuration. In a preferred embodiment, schematically shown in FIG. 3A, the imaging system 12A employs an infinite correction configuration, where the objective lens 13A collimates the light emitted from a source point located on the object plane O into a parallel beam, and a second lens 123 focuses the parallel beam to the surface of the detector 11. Other suitable optical components such as a waveplate 121 and a polarizer 122 may be provided between the objective 13A and the second lens 123. In an alternative embodiment, schematically shown in FIG. 3B, the imaging system 12B employs a finite correction configuration, where the objective lens 13B focuses the light from a source point on the object plane O to the surface of the detector 11. A second lens is not used. Other suitable optical components such as a waveplate 121 and a polarizer 122 may be provided between the objective 13B and the detector 11. The infinite correction configuration has a fixed magnification, while the finite correction configuration has a floating magnification. Note that the objectives 13A and 13B are only schematically shown in FIGS. 3A and 3B, while each objective may include a set of lenses.

Figures 3A, 3B:
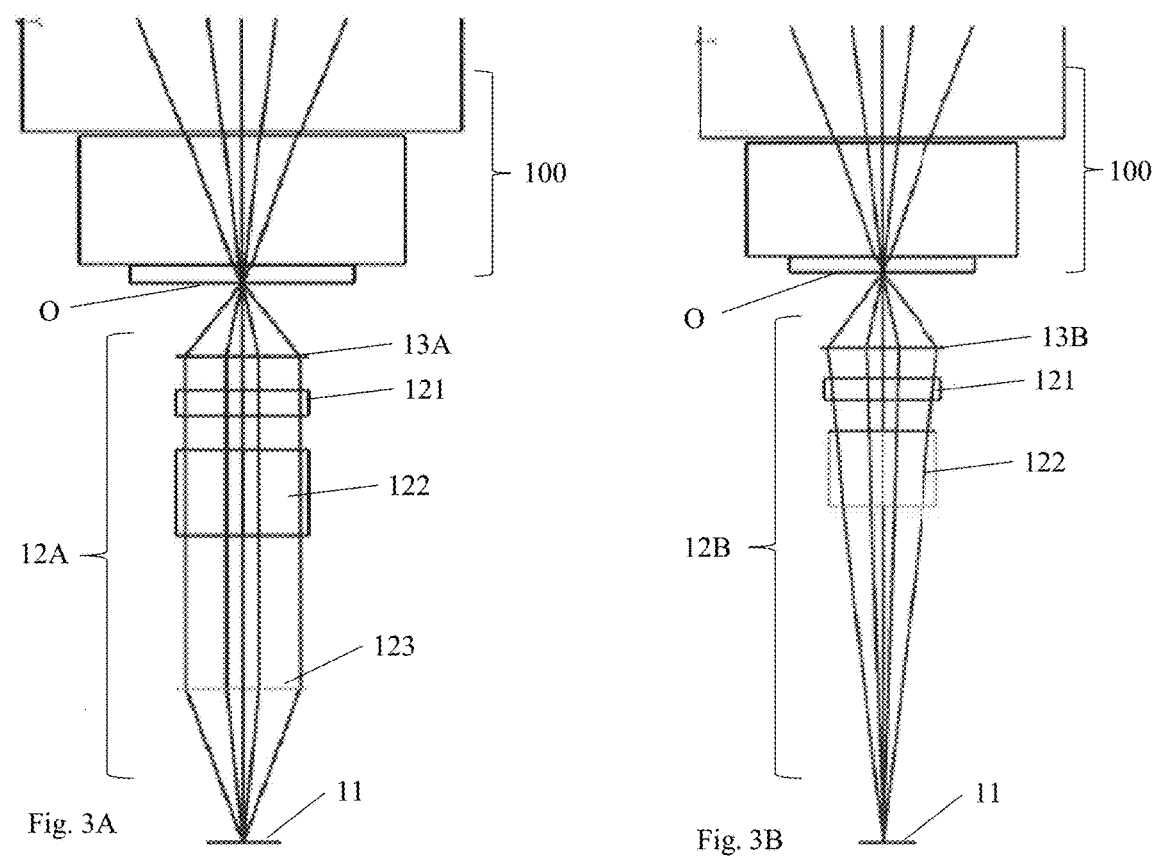
FIGS. 3A and 3B schematically illustrate two alternative optical configurations of the imaging system of the measurement apparatus according to embodiments of the present invention.

FIGS. 3A and 3B also schematically shows a part of the beam delivery system 100. In these examples, the laser beam is shown as being focused at the lower surface of the last lens (which may be a flat glass) of the beam delivery system.

For application in the focus spot size measurement apparatus, the infinite correction configuration is more preferred because it provides better point spread function, modulation transfer function and encircle energy, and correspondingly, lower aberration and higher resolution. Moreover, for the infinite correction configuration, adding optical components to the imaging system downstream of the objective does not add aberration, whereas it does in the finite correction configuration. Further, if an existing measurement apparatus is to be modified to measure smaller spot sizes, in the infinite correction configuration, only the objective 13A needs to be changed but the distance between the objective and the detector (and correspondingly, the physical housing for the optics) does not need to be changed, whereas in the finite correction configuration, both the objective and the distance between the objective and the detector (and correspondingly, the housing) need to be changed. In the finite correction configuration, the floating of the magnification, the working distance and the aberration are factors that may trade off with each other to give a slightly wrong spot size.

In one particular embodiment employing the infinite correction configuration and used with a water container, the objective 13 has a magnification of 63, a numerical aperture of 0.9, a free working distance of 2.4 mm, a cover glass thickness of 0 mm, a field of view of 23 mm, and a parfocal length of 45 mm.

Note that for simplicity, FIGS. 2, 3A and 3B do not show the liquid, but in embodiments of the present invention, a liquid such as water fills the optical path between the beam delivery system 100 and the objective 13.

Figure 4A:
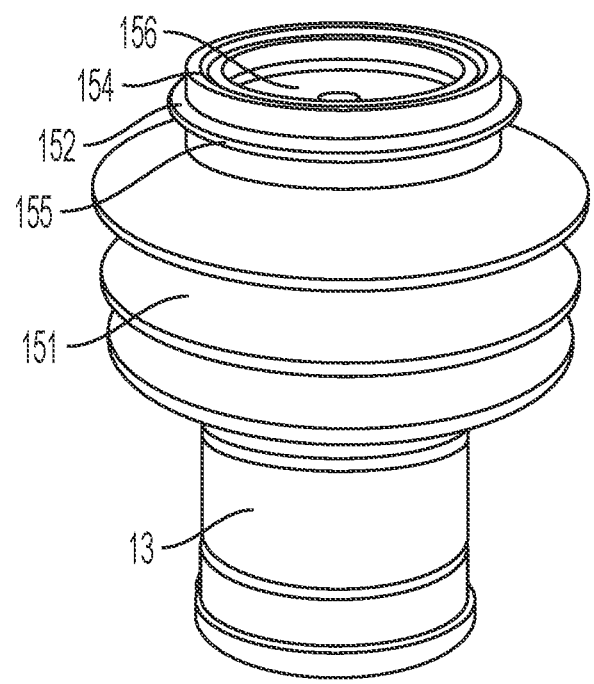
FIGS. 4A and 4B illustrate the structure of a liquid container of a measurement apparatus according to an embodiment of the present invention.
Figure 4B:
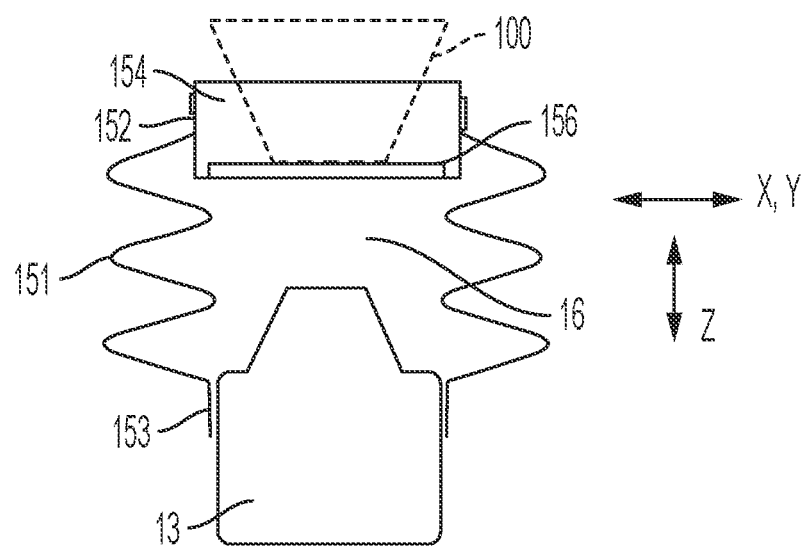

FIGS. 4A and 4B illustrate the structure of a liquid container 15 according to one embodiment of the present invention. FIG. 4A is a perspective image, and FIG. 4B is a schematic illustration of a cross-section, of the liquid container 15 joined with the objective 13. The liquid container 15 has a flexible body 151 with a top opening 152 and a bottom opening 153. The flexible body 151 may be made of any suitable material such as rubber, polyurethane or other plastics, etc. In a preferred embodiment, the body 151 has the shape of a bellows.

A window structure is secured to the top opening 152 of the body 151 in a liquid-tight manner. The window structure includes a rigid frame member (e.g. a ring) 154 and a transparent plate (e.g. glass plate or plastic plate) 156 joined to the frame to form a window. Any suitable structures may be used to secure the top opening with the window structure in a liquid-tight coupling. For example, the top opening may include a collar 152 formed of the same material as and integrally with the bellows, where the collar is placed around the rigid frame 154 and tied from the outside (for example by a tie 155 as seen in FIG. 4A), and/or glued to the rigid frame. An adapter ring or gasket made of a deformable material may be placed between the collar and the rigid frame to facilitate the liquid-tight seal between the frame and the top opening. The upper section of the rigid frame 154 may have a shape and structure configured to mechanically couple with a structure at the lower end of the beam delivery system 100.

The bottom opening 153 of the flexible body 151 is secured around a cylindrical section of the objective 13 in a liquid-tight manner. Any suitable structures may be used to secure the bottom opening with the objective, for example similar to those described above. The two openings are configured such that the surface of the objective 13 is substantially parallel to the glass plate 156.

The interior of the flexible body 151 is filled with water or another suitable liquid 16. As both the top and bottom openings are sealed in a liquid-tight manner, the entire container is liquid-tight, making it easy to handle. This enhances the usability and serviceability of the entire measurement apparatus.

In a preferred embodiment, the shape of the liquid container 15 is designed to prevent small air bubbles within the container from interfering with measurement. While the contained 15 should be filled as full as possible, small bubbles may form due to incomplete filling when the container is assembled, or may develop over time due to slow leakage or degassing of various plastic components. The liquid container 15 is shaped such that in the intended orientation during measurement, for example in the upright orientation as shown in FIGS. 4A and 4B or a in sideways orientation, the glass plate 156 is not located at the highest point of the container. As a result, during use, any air bubbles can be eliminated from the space between the glass plate 156 and the objective 13.

The overall size of the liquid container 15 is dictated by the size of the objective 13 and the relevant portions of the beam delivery system 100, as well as the designed distance between the surface of the objective 13 and the object plane. For example, the liquid container 15 may be designed such that the glass plate 156 is at or slightly beyond the object plane of the objective 13. In some embodiments, the liquid container 15 is approximately a few inches in diameter and a few inches tall.

The material and the physical parameters (e.g. wall thickness) of the flexible body 151 are chosen to ensure that the body has sufficient structural rigidity such that it can maintain its shape when no additional external force is applied, but can deform to a certain extent (e.g. by a few mm) in the axial direction (Z) and the transverse directions (X, Y), and can bend or twist, when sufficient forces are applied.

In use, the objective 13 is mounted on the housing 14 of the measurement apparatus, which in turn is mounted on a mechanical support structure allowing its position to be adjusted. The lower end of the objective of the beam delivery system 100 (schematically represented by the dashed line shape in FIG. 4B) is inserted through the rigid frame 154 and presses against the glass plate 156. The flexible body 151 allows the objective 13 and the beam delivery system 100 to be precisely aligned so that the laser focus spot is located at the desired position on the object plane for proper imaging by the imaging system 12. Alignment may be accomplished using mechanical structures of the laser beam delivery system and/or the mechanical support structure of the measurement apparatus. Any suitable mechanical structures may be used. In preferred embodiments, the amount of adjustment needed to align the beam delivery system 100 and the imaging system 12 is a new mm or less.

The image of the spot detected by the detector 11 is processed by a controller or data processing device 20 (see FIG. 1) coupled to the detector to determine the size of the detected image and calculate the size of the laser focus spot. The controller or data processing device may be, for example, a computer which includes processors and memories storing computer-readable program code which can be executed by the processors.

Figure 5:
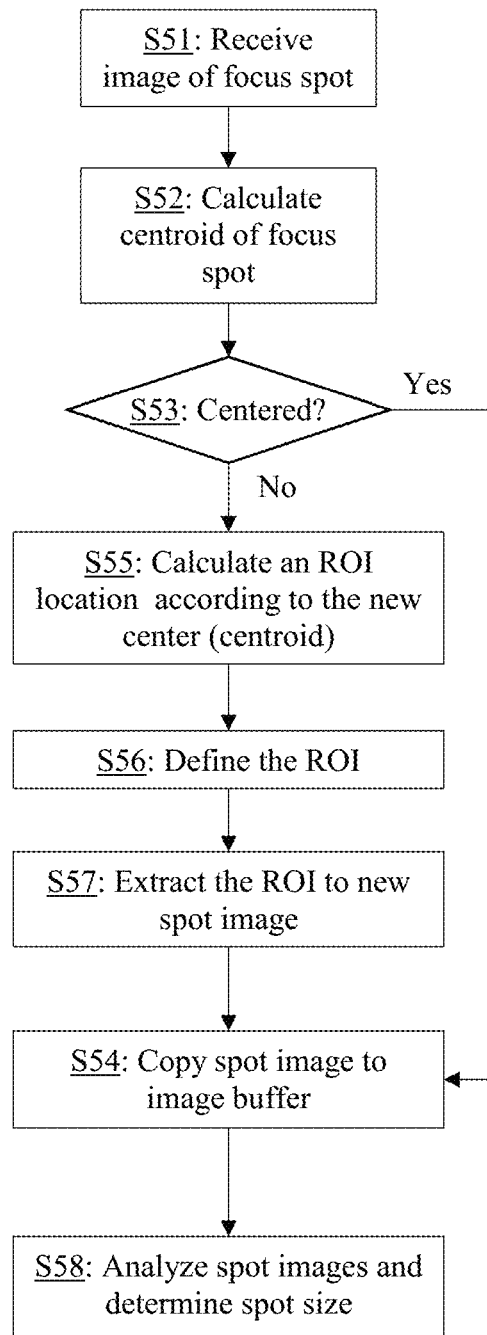
FIG. 5 schematically illustrates an image processing method employed by the measurement apparatus according to an embodiment of the present invention.

FIG. 5 schematically illustrates an image processing algorithm for analyzing the image detected by the detector 11 which corrects or minimizes the effect of ambient vibration. Such vibration causes small relative movements between the laser focus spot and the spot size measurement optics, which can significantly impact the accuracy of the spot size measurement when the laser focus spot size is on the order of 1 µm. As shown in FIG. 5, after the detector records an image of the focus spot (step S51), the centroid of the spot is calculated (step S52). It is then determined whether the spot (the centroid) is centered at a predetermined center location (step S53). If it is ("Yes"), the spot image is copied to an image buffer (step S54) and used as is in subsequent processing to calculate spot size. If the spot is not centered ("No"), the location of a region of interest (ROI) of the image is calculated according to the new center (the centroid position) (step S55), and the ROI is defined (step S56) and extracted to a new image (step S57). The new image, which contains the spot centered at the predetermined center location, is copied to the image buffer (step S54). Multiple images are taken over a period of time, and steps S51 to S57 are performed for each image. The spot images stored in the image buffer are then analyzed to calculate the laser focus spot size (step S58). This may be done, for example, by obtaining a light intensity profile of the spot image and determining the width of the profile at 50% maximum intensity. As mentioned earlier, the size of the laser focus spot may be calculated from the size of the spot image on the detector. In addition to spot size, the analysis may obtain other characteristics of the focus spot.

Although water is used in the above described embodiment as the content of the container 15, any other suitable liquid may be used such as an aqueous solution, etc.

It should be noted that the focus spot size measurement principle and the related optical system shown described above may also be used to measure the size of a laser focus spot located in water, they may also be used to measure the size of a laser focus spot located in other media, such glass, a piece of ex-vivo eye tissue such as cornea tissue and lens tissue.

It will be apparent to those skilled in the art that various modification and variations can be made in the laser focus spot size measurement apparatus and related method of the present invention without departing from the spirit or scope of the invention. Thus, it is intended that the present invention cover modifications and variations that come within the scope of the appended claims and their equivalents.

What is claimed is:

1. A measurement apparatus for measuring a laser focus spot size, comprising:
    a two-dimensional image detector having a detecting surface;
    an imaging system including at least an objective lens, the imaging system being disposed in front of the image detector and configured to form a magnified image of an object located on an object plane onto the detecting surface of the image detector; and
    a liquid container configured to contain a liquid and physically joined to the objective lens with a liquid-tight seal between the container and the objective lens, wherein a front optical surface of the objective lens is exposed to an interior of the container.

2. The measurement apparatus of claim 1, wherein the imaging system further includes a housing, wherein the objective lens is mounted at one end of the housing and the image detector is mounted at another end of the housing.

3. The measurement apparatus of claim 1, wherein the imaging system further includes a second lens disposed inside the housing in front of the image detector, wherein the objective lens is configured to collimate light emitted from a source point located on the object plane into a parallel light beam, and the second lens is configured to focus the parallel light beam to the detecting surface of the image detector.

4. The measurement apparatus of claim 3, wherein the objective lens has a numerical aperture NA between 0.7 and 1.0, and a lateral magnification between 50× and 100×.

5. The measurement apparatus of claim 4, wherein the image detector has a pixel size of 5 µm or less.

6. The measurement apparatus of claim 1, wherein the objective lens is configured to focus light emitted from a source point located on the object plane to the detecting surface of the image detector.

7. The measurement apparatus of claim 1, further comprising a data processing device connected to the image detector and configured to process image data generated by the image detector to determine a spot size of a light focus spot located at the object plane.

* * * * *